United States Patent [19]

Pozuelo

[11] Patent Number: 6,027,715
[45] Date of Patent: Feb. 22, 2000

[54] COMPOSITION AND MEANS FOR TREATING DRY MOUTH

[76] Inventor: Jose Pozuelo, Calle Virgen de la Salud, 78, 08024 Barcelona, Spain

[21] Appl. No.: 09/033,133

[22] Filed: Mar. 2, 1998

[51] Int. Cl.[7] ............... A61K 7/16; A61K 7/26; A61K 9/20; A61K 35/78; A61K 31/725

[52] U.S. Cl. ............ 424/49; 424/441; 424/464; 424/488; 424/58; 514/54; 514/777; 514/779; 514/783

[58] Field of Search ............... 424/49, 58, 441, 424/464, 488; 514/54, 779, 777, 783

[56] References Cited

U.S. PATENT DOCUMENTS

| | | | |
|---|---|---|---|
| 3,148,114 | 9/1964 | Fahrenbach et al. | 167/53 |
| 4,565,702 | 1/1986 | Morley et al. | 426/93 |
| 4,619,831 | 10/1986 | Sharma | 426/93 |
| 4,659,388 | 4/1987 | Inmami et al. | 514/781 |
| 4,744,986 | 5/1988 | Luber et al. | 424/156 |
| 4,869,902 | 9/1989 | Buehler et al. | 424/486 |
| 5,068,109 | 11/1991 | Foldager et al. | 424/441 |
| 5,099,009 | 3/1992 | Thibault et al. | 536/2 |
| 5,112,813 | 5/1992 | Luber et al. | 514/54 |
| 5,128,143 | 7/1992 | Baichwal et al. | 424/464 |
| 5,229,137 | 7/1993 | Wolfe | 424/687 |
| 5,288,507 | 2/1994 | Sims et al. | 424/682 |
| 5,614,207 | 3/1997 | Shah et al. | 424/440 |
| 5,656,284 | 8/1997 | Balkin | 424/435 |
| 5,681,827 | 10/1997 | Field | 514/54 |
| 5,776,491 | 7/1998 | Allen et al. | 424/465 |

FOREIGN PATENT DOCUMENTS 931148 of 1968 United Kingdom.

OTHER PUBLICATIONS

*Chondrus crispus*: Irish Moss, Carpageen Moss by Michael Guiry: Seaweed Information/NUIG, Oct. 26, 1998.

*Primary Examiner*—Shep K. Rose
*Attorney, Agent, or Firm*—Fay, Sharpe, Fagan, Minnich & McKee, LLP

[57] ABSTRACT

A tablet is disclosed for increasing the production of saliva in the human mouth. More specifically, a composition is described comprising a combination of organic compounds, insoluble in alkaline medium, combined with a retaining agent. The retaining agent is capable of absorbing and releasing saliva in aqueous solution such that when the compound is held in the oral cavity it remedies the condition of dry mouth.

16 Claims, No Drawings

COMPOSITION AND MEANS FOR TREATING DRY MOUTH

BACKGROUND OF THE INVENTION

Dryness of the mouth is a frequent disturbance affecting a major sector of the population, suffered by every person at one time or another. In some instances, it is so severe that it creates difficulty in the proper pronunciation of words, as the tongue actually sticks to the palate, at times with formation of fissures in the commissures of the mouth. It can also cause difficulty in tasting foods. Dryness of the mouth may result from the heightening of an individual's emotional state, such as when a person experiences anger or nervousness, or may be a permanent condition, such as with smokers. However, the major portion of the population tormented by this problem, and that to which this invention is directed, is that sector of the public who suffer from dryness of the mouth as a result of taking, on a daily basis, certain medications, such as anti-depressant drugs, anti-histamines, neuroleptics, and vasoconstrictors for example.

Further, halitosis of the mouth, which has long been thought to be caused by a malfunctioning of the stomach or the liver, is in most cases, a consequence merely of dryness of the mouth. It is caused by a decrease in the production of saliva in the mouth and the consequent incapacity to naturally wash the tongue, thus failing to remove the dead epithelia and degraded or broken down materials and giving a bad odor to expired air.

Chemically synthesized compounds are known that are available to relieve dryness of the mouth. However, the subject invention contemplates the use of a combination of naturally occurring substances to accomplish this task.

Accordingly, it has now been found, that the combination of certain natural products, as disclosed herein, can increase the production of saliva and alleviate the symptoms mentioned hereinabove.

It is, therefore, an object of this invention to provide a composition which, when placed in the oral cavity has the effect of increasing salivation.

It is a further object to provide a tablet easily held in the mouth over an extended period of time, without impeding speech, which has the effect of increasing salivation.

It is yet another object of the invention to produce the saliva-increasing tablet from naturally occurring compounds.

These and other objects of the invention, readily understood by those skilled in the art, will become apparent from the following description of the invention and the claims appended thereto.

SUMMARY OF THE INVENTION

In a first aspect, the present invention provides a composition for increasing the production of saliva in an individual's mouth. The composition preferably comprises an algae component and a pectin-rich component having relatively low water solubility properties.

In another aspect, the present invention provides a tablet for reducing the condition of dry mouth. The tablet preferably comprises an algae component and a pectin-rich component.

In yet a further aspect, the present invention provides a method for alleviating dryness of mouth. The method comprises providing a tablet including an algae component and a pectin-rich component; placing the tablet in an individual's mouth; and maintaining the tablet in the person's mouth whereby the production of saliva is increased and a portion of the produced saliva is retained by the tablet.

DESCRIPTION OF THE PREFERRED EMBODIMENTS

In accordance with the present invention, a composition is provided for increasing moisture in the mouth. The preferred embodiment composition comprises an algae component possessing water-absorbing properties and a low water solubility, pectin-rich organic component. These agents are preferably combined in a tablet such that when the tablet is placed in one's mouth saliva is absorbed by osmosis and retained in the tablet by the algae component and subsequently liberated when the concentration of saliva in the oral cavity decreases. The present invention also relates to the use of a combination of proteins and other naturally occurring compounds, that when properly combined, increase the production of saliva in the mouth, thereby curing the condition of dryness of the mouth.

There are three fundamental factors associated with the preferred embodiment tablet, composition, and technique. The first factor pertains to the saliva produced by the human mouth. The second factor relates to particular types of algae having special properties. The third factor concerns a group of organic and naturally-existing compounds exhibiting high insolubility in alkaline solutions, specifically in saliva.

The saliva produced by the human mouth is well known to be an aqueous, odorless, and alkaline medium of viscous consistency. Saliva is secreted by three glands in the mouth. The parotid salivary glands are located on each side of the face in the interior aspect of the cheek in front of the second upper molar. The submandibular gland has its opening beside the frenulum of the tongue. The sublingual gland has its opening on the floor of the mouth behind the lower frontal teeth. The physical aspects and composition of the saliva of each one of these three glands is slightly different and the amount of saliva produced by each gland is variable depending upon various factors, such as the quality of the food ingested, the emotional state of the person, and other factors.

The average daily amount of saliva produced by all three glands together is around 1,500 cc, with variations in amount as just stated hereinabove. Among the many functions that the saliva performs are: increasing the wetness and softness of food in preparation for its progress down to the stomach; facilitation in the mouth and in the stomach of the action of gastric fluid; initiation of saccharification of starches; increasing the palatable taste of food; contribution to the masticatory function; and, abolition of dryness of the mouth.

The algae component of the preferred embodiment composition and tablet described herein, plays a fundamental role. The algae component absorbs and retains saliva upon secretion by the salivary glands, and excretes the retained saliva when the mouth becomes particularly dry. The preferred algae contemplated for use herein is Chondrus Crispus, commonly known as "Irish Musgo" because of its similar appearance to the lichen of Ireland. This algae is also known as "Botelho-Crespo" because of the narrowness and dilatation of its stems, similar in shape to glass bottles, and "Botelho-Rino" because of the frequent stem segments in "Y" shape and a cartilagineous structure, which makes it similar to the ethmoid bone of the nose. The active ingredient of the Chondrus Crispus with respect to this invention is the protein compounds contained in the algae. These compounds are phycoerytrina and phycocyanine. These proteins are characterized by their ability to absorb water, or saliva, by osmosis and to create a mucilage which contains 80% water. Therefore, the preferred embodiment algae absorbs and retains water, or saliva, such that in the presence of the remaining natural compounds a coagulation is formed which contains 80% (by total volume of the compound) water. Other types of algae may be utilized such as for example, algae obtained from the sea in Galicia, Portugal. This and other suitable algae may also be obtained from an array of commercially available sources.

Chondrus Crispus exists in large amount on the shores of northern Ireland and also on the rocky coast of the Gulf of Cantabrico in north Spain. The algae grows in cool seawater from the Cantabric Sea to the southern coast of Portugal on the Atlantic shore. Not all Chondrus Crispus leaves are of the same good quality. In fact, it has been found that while the leaves produced in warm waters off the south coast of Portugal do not absorb more than 40% of their dried volume, the leaves of the algae from the cold waters of the Cantabric Sea may absorb up to 90% of their dried volume. The leaves are collected during low tide and those leaves which maintain good color and appear healthy are washed in river water and left to dry in the sun. Once dried by the sun, the whole plant is triturated and reduced to a smooth powder to be mixed with the organic and natural compounds.

The organic and natural substances utilized in the preferred embodiments of the present invention have three common properties. First, they are highly insoluble in alkaline solutions, such as saliva, and easily destroyed in acidic solutions, such as stomach fluids. Second, they are found as natural substances in natural vegetation and are edible and non-toxic. Third, they are rich in pectin. It is known that the main component of pectin is "Pectose", which is almost totally insoluble in alkaline water or saliva.

Pectin forms part of the skins of many fruits and vegetables, and is insoluble in weak alkaline solutions and highly soluble in hydrochloric acid. Pectin is moderately water soluble in water of pH 7.0. However, as noted, pectin is essentially insoluble in alkaline water or saliva. Therefore, the compounds are easily destroyed in the gastric fluid of the stomach if totally ingested. A wide array of other compounds or agents can be utilized instead of, or in addition to, pectin. Suitable agents are nontoxic; insoluble in saliva (or alkaline aqueous solutions); and soluble in relatively acidic solutions such as the gastric environment of the stomach.

Many other possible compounds, natural and synthetic, could be used to fulfill the role of the agents described herein. However, those disclosed herein have been selected so that the resulting product not only relieves dryness of the mouth and the halitosis which frequently accompanies such dryness of the mouth, but it is also palatable and nontoxic if swallowed.

The organic compounds rich in pectin, highly insoluble in saliva, cause the salivary glands to increase the production of saliva in an attempt to dissolve the pellets or tablets. The particles of algae which are mixed with the pectin-rich organic compounds in the tablets attract and absorb the saliva through an osmosis process to form a mucilage. The mucilage absorbs and releases water according to the condition of the mouth (i.e. wet or dry). The mucilage typically absorbs water in an amount equal to about 80% or more of its volume (i.e. volume prior to the addition of water).

The saliva non-soluble pectin-rich compound continues stimulating the salivary glands to produce more saliva, in a physiological response of the salivary gland to dilute the solid compound. Then, the individual may opt to swallow the saliva produced or to swallow the tablet upon which the salivary action stops. As will be understood, it is possible to re-establish such action when needed by taking another tablet. As a consequence, the mouth is maintained wet by the production of saliva at will. The 80% water absorbed, by the algae part of the tablet, prevents the tablet from becoming dry and sticking to palate or teeth. This results in the ability to stimulate the production of saliva at will so that the tongue is always wet and able to wash the detritus off its surface and to eliminate otherwise resulting halitosis.

The present invention also provides a method for alleviating, or at least reducing the discomfort associated with, heartburn, by use of the preferred embodiment tablets. In accordance with this aspect of the present invention, an individual suffering from heartburn places a tablet, as described herein, in his or her mouth. The tablet is maintained in the individual's mouth, whereby the production of saliva is increased. The increased production of saliva passes through the individual's esophagus and reduces heartburn.

The algae component and the organic pectin-rich component may be combined in nearly any composition in accordance with the preferred embodiment composition, tablet, and method described herein. Typically, the algae component and the organic pectin-rich component are combined in a particular weight ratio to one another. For example, a typical ratio (by weight) of algae component to the organic pectin-rich component may range from about 0.5 to about 40 parts by weight of the algae component to about 10 parts by weight of the organic pectin-rich component. Preferably, the weight ratio ranges from about 1 to about 20 parts of algae component to about 10 parts of the organic pectin-rich component. It will be understood that the present invention includes the use of greater or lesser ratios of algae and pectin-rich components.

The preferred embodiment tablets preferably result from the compression of a fine powder ground from the algae particles and organic compounds. The preferred embodiment tablets should be no larger than approximately 3.5 millimeters, and are preferably about 2.5 millimeters in diameter and about 2 millimeters in thickness, such that the tablet can be hidden under the tongue, placed between the upper jaw mucous and the cheek, or maintained by the tongue against the floor of the mouth. These positions are where the salivary glands open into the mouth, thus affording maximum absorption of water or saliva by the algae and providing maximum stimulation for production and flow of saliva. Further, in these positions, there is minimal obstruction in the mouth while attempting to continue normal conversation.

The organic compounds used herein were selected to create a composition having a good taste. However, any number of organic compounds insoluble in water or saliva and rich in pectin may be used. In this instance, sweet almonds, seeds of olives, seeds of pine nut, and corn peel have been combined with the algae. All of the foregoing substances are first ground to a smooth powder. It is preferred that the algae is ground to powder in the same manner as the pectin-containing compounds. Further, in order to improve the final taste of the tablet to be produced and to offer a variety of flavors, the powder with the triturated particles of algae may be combined with one or more flavoring agents or flavor enhancers. One or more natural extracts of strawberry, mint, raspberry, and lemon syrups, may be blended with the resulting mixture until acquiring a uniform taste and color. The resulting composition is then preferably compressed by techniques known in the art to produce a tablet, most preferably in the form of a lentil.

The following Example demonstrates the production and use of the preferred embodiment tablet described herein. It will be noted, however, that while specific compounds and process parameters are exemplified herein, such are presented merely to aid the practitioner in further understanding the invention, and are not intended to be limitative thereof. The invention is to be accorded the full breadth of the claims appended hereto.

EXAMPLE

Pills corresponding to the subject invention were produced in the following manner:

The alkaline-insoluble, pectin-rich organic compounds listed below (nonpalpable grains) were prepared by grinding each of the compounds to a smooth powder to make a tablet with a diameter of about 2.5 mm and 2 mm in thickness.

| Organic Compound | Amount in Milligrams |
|---|---|
| Sweet Almonds | 250.000 |
| Seed of Olives | 40.000 |
| Seed of Pine Nut | 20.000 |
| Corn Peel | 40.000 |

These powders were added to 150 milligrams of Chondrus Crispus algae. This algae had been previously collected during low tide and the complete plant pulled out of the ground. Leaves were washed in clean river water and left to dry in the sun. Once dried by the sun, the whole plant was triturated and reduced to a smooth powder. Further to this combination was added a variety of flavor-enhancing substances of the natural extracts of strawberry, mint, raspberry, and lemon syrups in powdered form. This mixture of powders was blended until a uniform taste and color was acquired. This mixture was slightly pasty. This pasty mixture was then submitted to a high compression presser in order to obtain a tablet of 1.75 mm by 2.5 mm, which was roughly ½₀ of its uncompressed volume. The tablet resembled a lentil or flat seed.

The invention has been described with reference to the preferred embodiments. Obviously, modifications and alterations will occur to others upon a reading and understanding the preceding detailed description. It is intended that the invention be construed as including all such modifications and alterations in so far as they come within the scope of the appended claims or the equivalents thereof.

What is claimed is:

1. A composition for increasing the production of saliva in an individual's mouth, said composition consisting essentially of:
   an algae component having water-absorbing properties; and
   a pectin-rich component having relatively low water solubility properties.

2. The composition of claim 1 wherein said algae component includes Chondrus Crispus algae.

3. The composition of claim 1 wherein said algae component comprises at least one of phycoerytrina and phycocyanine.

4. The composition of claim 3 wherein said algae component comprises both phycoerytrina and phycocyanine.

5. The composition of claim 1 wherein said pectin-rich component is derived or obtained from a naturally occurring substance.

6. The composition of claim 1 wherein said pectin-rich component is highly insoluble in alkaline solutions.

7. The composition of claim 1 wherein said pectin-rich component is highly soluble in acidic solutions.

8. The composition of claim 1 wherein upon addition of water to said composition, said algae component and said pectin-rich component absorb water in an amount of at least 80% of the total volume of said algae component and said pectin-rich component.

9. The composition of claim 1 wherein said algae component and said pectin-rich component are in a ratio to each other of from about 0.5 to about 40 parts by weight of said algae component to about 10 parts by weight of said pectin-rich component.

10. The composition of claim 9 wherein said algae component and said pectin-rich component are in a ratio to each other of from about 1 to about 20 parts by weight of said algae component to about 10 parts by weight of said pectin-rich component.

11. A tablet for reducing the condition of dry mouth, said tablet consisting essentially of:
   from about 0.5 to about 40 parts by weight of an algae component; and
   about 10 parts by weight of a pectin-rich component.

12. The tablet of claim 11 wherein said algae component includes at least one of phycoerytrina and phycocyanine.

13. The tablet of claim 11 wherein the ratio of said algae component to said pectin-rich component ranges from about 1 to about 20 parts by weight of said algae component to about 10 parts by weight of said pectin-rich component.

14. A tablet for increasing moisture in the mouth consisting essentially of from about 0.5 to about 40 parts by weight of an algae component possessing water-absorbing properties and about 10 parts by weight of at least one water insoluble, pectin-rich organic compound, combined such that saliva in the oral cavity is absorbed by osmosis and retained by said algae component and subsequently liberated when the concentration of saliva in the oral cavity decreases.

15. A method for alleviating dryness of mouth, said method comprising:
   providing a tablet consisting essentially of (i) an algae component, and (ii) a pectin-rich component;
   placing said tablet in an individual's mouth; and
   maintaining said tablet in said mouth, whereby the production of saliva is increased and a portion of said produced saliva is retained by said tablet.

16. A method for increasing the passage of alkaline saliva through the esophagus, said method comprising:
   providing a tablet consisting essentially of (i) from about 0.5 to about 40 parts by weight of an algae component, and (ii) about 10 parts by weight of a pectin-rich component; and
   placing said tablet in said mouth, whereby the production of saliva is increased and a portion of said produced saliva is retained by said tablet.

* * * * *